United States Patent [19]

Braid

[11] 4,153,563
[45] May 8, 1979

[54] LUBRICANT COMPOSITIONS CONTAINING BENZOTRIAZOLE-ALLYL SULFIDE REACTION PRODUCTS

[75] Inventor: Milton Braid, Westmont, N.J.

[73] Assignee: Mobil Oil Corporation, New York, N.Y.

[21] Appl. No.: 909,222

[22] Filed: May 24, 1978

[51] Int. Cl.$^2$ .................. C10M 1/38; C07D 249/18
[52] U.S. Cl. ..................................... 252/47; 252/402; 260/308 B
[58] Field of Search .............. 252/47, 402; 260/308 B; 44/63

[56] References Cited

U.S. PATENT DOCUMENTS

| | | | |
|---|---|---|---|
| 3,265,620 | 8/1966 | Heiman | 252/49.3 X |
| 3,527,704 | 9/1970 | Perilstein et al. | 252/49.7 |
| 3,531,414 | 9/1970 | Randell et al. | 252/47 X |
| 3,884,932 | 5/1975 | Andress, Jr. | 260/308 B |
| 3,897,351 | 7/1975 | Davis et al. | 252/49.3 X |
| 4,014,894 | 3/1977 | Andress, Jr. | 260/308 B |
| 4,107,060 | 8/1978 | Schick et al. | 252/49.3 |

OTHER PUBLICATIONS

Maeda et al., CA 85:35375h (1976).

*Primary Examiner*—Thomas Waltz
*Attorney, Agent, or Firm*—Charles A. Huggett; Raymond W. Barclay; Thomas S. Szatkowski

[57] ABSTRACT

Lubricant compositions containing oleaginous materials and, in amounts sufficient to impart resistance to oxidation and metal corrosion thereto, reaction products of a benzotriazole compound and an organic sulfur containing compound selected from the group consisting of α and β substituted allyl sulfides and disulfides, and sulfurized olefins, having reactive unsaturated bonds.

24 Claims, No Drawings

LUBRICANT COMPOSITIONS CONTAINING BENZOTRIAZOLE-ALLYL SULFIDE REACTION PRODUCTS

BACKGROUND OF THE INVENTION

1. Field of the Invention

The invention relates to oleaginous compositions normally susceptible to the oxidative deterioration and metal corrosion. In particular, the invention relates to compositions such as mineral and synthetic lubricating oils, gear oils, transmission fluids, greases and other oleaginous compositions normally requiring the presence of antioxidant or anticorrosion additives.

2. Description of the Prior Art

Prior to the present invention, triazoles have been employed in lubricant compositions as metal deactivators. For example, U.S. Pat. No. 3,597,353 of Randell et al. discloses the use of 4, 5, 6, 7-tetrahydrobenzotriazole as a metal deactivating additive for natural and synthetic lubricants. Similarly, U.S. Pat. No. b 3,413,227 of Howard et al. teaches that an alkyl-substituted benzotriazole where the alkyl group contains from 2 to 20 carbon atoms can be used as a corrosion or tarnish inhibitor.

In U.S. Pat. No. 4,060,491, Bridger et al. teach the utilization of 5-alkylbenzotriazoles, in which the alkyl group contains from 4 to 16 carbon atoms, in a method for reducing wear between moving steel-on-steel surfaces.

In U.S. Pat. No. 3,788,993 of Andress, it is taught that benzotriazoles react with alkyl or alkenylsuccinic anhydrides to form reaction products which impart corrosion inhibiting properties to lubricating oils.

Nnadi et al., in U.S. Pat. No. 4,048,082 discloses that esters of adducts of benzotriazole and unsaturated dicarboxylic acids or anhydrides thereof impart antirust properties to organic compositions.

None of the prior art patents disclose the novel reaction products of the present invention.

SUMMARY OF THE INVENTION

It has now been found that the reaction product of a benzotriazole compound and an organic sulfur containing compound selected from the group consisting of $\alpha$ and $\beta$ substituted allyl sulfides and disulfides, and sulfurized olefins having reactive unsaturated bonds, imparts improved antioxidant and anticorrosion properties to the oleaginous compositions to which it is added.

The benzotriazole compounds which are utilized to form the reaction products of the present invention are described by the formula:

where R is hydrogen or a hydrocarbyl group containing from 1 to about 12 carbon atoms.

Preferred are benzotriazoles in which R is hydrogen or an alkyl group containing from 1 to about 8 carbon atoms.

Particularly preferred are benzotriazole and toluotriazole.

The $\alpha$ and $\beta$ substituted allyl sulfide and disulfide compounds which are utilized to form the reaction products of the present invention have the formula:

$$R'C=C-CH_2-S-CH_2-C=CR'$$
$$\quad H \ R \qquad\qquad R \ H$$

and $$R'C=C-CH_2-S-S-CH_2-C=CR'$$
$$\quad H \ R \qquad\qquad\qquad R \ H$$

where R and R' are selected from the group consisting of hydrogen, alkyl having from 1 to 8 carbon atoms, aryl and aralkyl having from 6 to about 14 carbon atoms. Those of skill in the art will be aware that R and R' may be the same or different.

Preferred are hydrogen, alkyl having from 1 to about 4 carbon atoms, aryl and aralkyl having from 6 to about 12 carbon atoms.

Particularly preferred are allyl sulfide, allyl disulfide, methallyl sulfide, methallyl disulfide, propallyl sulfide, propallyl disulfide, phenallyl sulfide and phenallyl disulfide.

These $\alpha$ and $\beta$ substituted allyl sulfides and disulfides can be prepared by reaction of allyl halides e.g., methallyl chloride or $\alpha$-chloromethylstyrene with an alkali metal sulfide or disulfide e.g., sodium sulfide or sodium disulfide. Alternatively, the disulfide can be prepared by reacting the allyl halides with an alkali metal thiosulfate (e.g. sodium thiosulfate) to form the Bunté salt and subsequent reaction with a base e.g. sodium hydroxide.

As used herein, the term sulfurized olefin refers to an organic sulfide and disulfide containing composition which is produced by sulfohalogenating an olefin with a sulfur halide in the presence of a catalytic quantity of a lower aliphatic alcohol to form a sulfohalogenated organic intermediate, and thereafter sulfurizing and dehalogenating the intermediate in the presence of a substantial quantity of a lower aliphatic alcohol by treatment with an aqueous alkali metal monosulfide solution. U.S. Pat. No. 3,707,502 of Horodysky, the enire contents of which are incorporated by reference, describes the method of producing sulfurized olefins in greater detail.

These sulfurized olefins compounds are characterized by the presence of one or more reactive unsaturated bonds.

Horodysky in U.S. Pat. No. 3,707,505 and Meyers in U.S. Pat. Nos. 3,471,404 and 3,697,499 also describe sulfurized olefins and methods for their preparation. The contents of each of these patents is incorporated herein by reference.

These references disclose that the sulfurized olefins are formed from a wide variety of olefinic substances. All of these can be used to form the reaction products of the present invention. However, it is preferred that sulfurized olefins produced from olefins having 3 or 4 carbon atoms be employed. Of these, most preferred is sulfurized isobutylene.

In general the reaction products of the present invention are formed by reacting the benzotriazole compound with the organic sulfur containing compound in proportions (expressed as the molar ratio: benzotriazole compound: organic sulfur containing compound) of from about 0.25:1 to about 10:1. Preferred are molar ratios of from about 0.5:1 to about 2.5:1.

Reaction temperature of from about 5° C. to about 150° C. are utilized, with from about 25° C. to about 125° C. being preferred. Generally, the reactants are contacted for about 0.25 to 16 hours, with from about 0.5 to about 2 hours being preferred. As those of skill in the art are aware, the particular reaction times utilized depend on the temperature and the particular reactants utilized. Generally, for a given pair of reactants, the reaction time at higher temperatures may be shorter than if lower temperatures are employed.

The reaction is catalyzed by the presence of an acidic material. Suitable materials include hydrogen sulfide, hydrogen chloride, methanesulfonic acid, and p-toluenesulfonic acid.

A preferred catalyst is p-toluenesulfonic acid.

The reaction product may be used in lubricant compositions of the present invention in its entirety. Alternately, it has been found that the reaction product can be fractionated by any method and the fractions utilized in the lubricant composition. Particularly, the reaction product can be fractionated by distillation, filtration, crystallization, partition freezing, chromotography, or extraction with various solvents such as petroleum ether, cyclohexane, ether, acetone, or ethyl acetate.

Of particular significance in accordance with the present invention is the ability to improve the resistance to oxidation and corrosion of oleaginous materials such as lubricating media, which may comprise a lubricating oil in the form of either a mineral oil or a synthetic oil, or in the form of a grease in which any of the aforementioned oils are employed as a vehicle. In general, mineral oils, both paraffinic, napthenic and mixtures thereof, employed as the lubricant, or grease vehicle, may be of any suitable lubricating viscosity range, as for example, from about 45 SSU at 100° F. to about 6000 SSU at 100° F., and preferably, from about 50 to about 250 SSU at 210° F. These oils may have viscosity indexes ranging to about 100 or higher. Viscosity indexes from about 70 to about 95 are preferred. The average molecular weight of these oils may range from about 250 to about 800. Where the lubricant is to be employed in the form of a grease, the lubricating oil is generally employed in an amount sufficient to balance the total grease composition, after accounting for the desired quantity of the thickening agent, and other additive components to be included in the grease formulation. A wide variety of materials may be employed as thickening or gelling agents. These may include any of the conventional metal salts or soaps, which are dispersed in the lubricating vehicle in grease-forming quantities in such degree as to impart to the resulting grease composition the desired consistency. Other thickening agents that may be employed in the grease formulation may comprise the non-soap thickeners, such as surface-modified clays and silicas, aryl ureas, calcium complexes and similar materials. In general, grease thickeners may be employed which do not melt and dissolve when used at the required temperature within a particular environment; however, in all other respects any material which is normally employed for thickening or gelling hydrocarbon fluids for forming grease can be used in preparing the aforementioned improved grease in accordance with the present invention.

In instances where synthetic oils, or synthetic oils employed as the vehicle for the grease, are desired in preference to mineral oils, or in combination therewith, various compounds of this type may be successfully utilized. Typical synthetic vehicles include polyisobutylene, polybutenes, hydrogenated polydecenes, polypropylene glycol, polyethylene glycol, trimethylol propane esters, neopentyl and pentaerythritol esters, di(2-ethylhexyl) sebacate, di(2-ethylhexyl) adipate, dibutyl phthalate, fluorocarbons, silicate esters, silanes, esters of phosphorous-containing acids, liquid ureas, ferrocene derivatives, hydrogenated mineral oils, chain-type polyphenyls, siloxanes and silicones (polysiloxanes), alkyl-substituted diphenyl ethers typified by a butyl-substituted bis (p-phenoxy phenyl) ether, phenoxy phenylethers.

It is to be understood, however, that the compositions contemplated herein can also contain other materials. For example, extreme pressure agents, viscosity index agents, coantioxidants, antiwear agents, antirust agents, and the like can be used. These materials do not detract from the value of the compositions of this invention, rather these materials serve to impart their customary properties to the particular compositions in which they are incorporated.

Mineral oil heat-exchange fluids particularly contemplated in accordance with the present invention have the following characteristics: high thermal stability, high initial boiling point, low viscosity, high heat-carrying ability and low corrosion tendency.

Further, transmission fluids which are of consequence to the present invention are blends of highly refined petroleum base oils combined with VI improvers, detergents, defoamants and special additives to provide controlled-friction or lubricity characteristics. Varied transmission design concepts have led to the need for fluids with markedly different frictional characteristics, so that a single fluid cannot satisfy all requirements. The fluids intended for use in passenger car and light-duty truck automatic transmissions are defined in the ASTM Research Report D-2: RR 1005 on "Automatic Transmission Fluid/Power Transmission Fluid Property and Performance Definition" Specifications for low-temperature and aircraft fluids are defined in U.S. Government Specification MIL-H-5606A.

The oxidative and corrosion resistance of functional fluids such as hydraulic fluids can also be improved by the addition of the reaction products of the present invention.

In general, the reaction products of the present invention may be employed in the oleaginous material in any amount which is effective for imparting the desired degree of oxidation or corrosion resistance thereto. In many applications, the additive is effectively employed in amounts from 0.01 to 10% by weight, and preferably from 0.1 to 5% by weight of the total weight of the composition.

DESCRIPTION OF SPECIFIC EMBODIMENTS

The following examples and comparative data will serve to illustrate the novel reaction products of the present invention and the marked improvement in antioxidant and anticorrosion properties of oleaginous materials containing these reaction products or fractions thereof. It will be understood, however, that it is not intended that the invention be limited to the particular composition described herein. Various modifications can be employed as will be readily apparent to those skilled in the art.

EXAMPLE 1

Reaction of Benzotriazole with Methallyl Sulfide

Benzotriazole (59.5 g.) and methallyl sulfide (35.6 g.) in 100 ml of xylene were heated at 122° C. with refluxing. No reaction could be detected by gas chromatogrpahy. To the reaction mixture about 0.1 g. of p-toluenesulfonic acid was added and the reflux temperature rose to 138° C. during 0.25 hr. as gas chromatography concurrently showed the formation of reaction products. After refluxing for 7.5 hr. at about 138° C., the reaction mixture was washed with aqueous sodium carbonate solution, followed by water, and then dried. Solvent was removed by rotary evaporation and a white solid reaction product, m.p. 136°-138° C., was obtained by recrystallization from 2-propanol. The infrared spectrum of this product showed no unsaturation, indicating di-addition and the presence of strong gem-dimethyl absorptions suggested substantial Markovnikoff addition. Elemental analysis was also in agreement with formation of a di-adduct:

| Analysis (Wt. %) | C | H | N | S |
|---|---|---|---|---|
| Calculated for di-adduct ($C_{14}H_{19}N_3S$) | 63.13 | 6.36 | 22.09 | 8.43 |
| Found | 62.80 | 6.24 | 20.68 | 7.70 |

From the mother liquor of the solid product there as obtained by column chromatography over neutral alumina with benzene eluent an oil addition product which gas chromatography showed was free of benzotriazole and consisted of an isomeric mixture of addition products.

EXAMPLE 2

The procedure of Example 1 was repeated except that (0.1 gram) of potassium t-butoxide catalyst was substituted for the p-toluenesulfonic acid catalyst used in Example 1. Little or no reaction could be detected at 120° C. when using the potassium t-butoxide catalyst. This indicated the criticality of utilizing an acid catalyst to form the reaction products of the present invention.

EXAMPLE 3

Methallyl Disulfide - Benzotriazole Addition Products

Benzotriazole ( 11.9 g.), methallyl disulfide (8.7 g.) and p-toluenesulfonic acid ( 0.1 g.) in about 75 ml. of xylene were heated, forming a clear homogeneous solution. This solution was heated for more than 12 hr. at 145° C. while small aliquot samples were withdrawn periodically and examined by gas chromatography. The appearance of addition products peaks was observed concurrently with the consumption of the reactants, benzotriazole and methallyl disulfide. Xylene solvent was removed by rotary evaporation. The residue was distilled in a Kugelrohr apparatus at less than 0.1 mm. of mercury pressure. A small amount of distillate product ( 1 g.) was collected; the residue mixture of products was a dark amber very viscous oil. The infrared spectrum of the reaction product mixture showed the doublet absorption ( 1385, 1375 $cm^{-1}$) and the substantial disappearance of the strong terminal vinyl C—H deformation band (900 $cm^{-1}$) both indicating addition to the olefin groups of the reactant methallyl disulfide.

The mixture of addition products was fractionated by extraction with cyclohexane. Removal of the cyclohexane left a very viscous reddish oil which had the gem-dimethyl doublet in the infrared spectrum and still had some unsaturation indicated by the presence of a weak-medium 900 $cm^{-1}$ band.

| | C | H | N | S |
|---|---|---|---|---|
| Analysis | 55.58 | 5.96 | 16.28 | 23 |

EXAMPLE 4

Benzotriazole (59.5 grams) and sulfurized isobutylene (180 grams) which was prepared as described in U.S. Pat. No. 3,707,504 were reacted in 100 ml. of xylene solvent at 135° C. under a nitrogen atmosphere for a total of 10 hrs. The catalyst was p-toluenesulfonic acid (0.2 g.).

The product was a dark viscous oil which contained amounts of insoluble material, believed to be unreacted benzotriazole. Infrared spectroscopy of the product showed almost complete disappearance of the unsaturated bonds present in the sulfurized isobutylene reactant.

In order to demonstrate the efficacy of the various fractions of the reaction products of this invention, the product was filtered to remove insoluble excess benzotriazole. The filtered product was further fractioned by extraction with petroleum ether and cyclohexane.

PRODUCT EVALUATIONS

The reaction products and fractions thereof as produced in the above examples were tested for antioxidant and anticorrosion activity.

For the oxidation test, the reaction products were blended into a neutral solvent refined mineral base oil having a viscosity at 100° F. of 130 SUS. The oils were then subjected to a stream of air at the rate of 10 liters per hour at a temperature of 325° F. for 40 hours in the presence of metals having pro-oxidant properties: iron, copper, lead and aluminum. The lead sample was weighed before and after the test, since lead is one of the metals more susceptible to corrosion by oxidation. The test measurements are change in acidity or neutralization number (Δ NN) as measured by ASTM D-974, change in kinematic viscosity at 210° F. (Δ KV) lead loss in milligrams, and sludge. Results of the test are presented in Table 1.

TABLE 1

| CATALYTIC OXIDATION TEST 325° F., 40 HOURS | | | | |
|---|---|---|---|---|
| Base Oil | ΔNN | ΔKV | Pb Loss, mg | Sludge |
| Base oil without additive | 17 | 334 | 66 | Heavy |
| Example 1 | | | | |
| Solid Product | | | | |
| Base oil + 1 wt % solid product | 5.7 | 54 | 36.4 | Moderate |
| Base oil + 0.5 wt % solid product | 1.1 | 13 | 26.7 | Moderate |
| Base oil + 0.25 wt % solid product | 10.1 | 166 | 64.2 | Moderate |
| Oil Product | | | | |
| Base oil + 1 wt % oil product | 1.9 | 18 | 20.2 | Heavy |
| Base oil + 0.5 wt % oil product | 2.4 | 15 | 28.8 | Heavy |
| Base oil + 0.25 wt % oil product | 1.8 | 155 | 84 | Moderate |
| Example 3 | | | | |

TABLE 1-continued

CATALYTIC OXIDATION TEST 325° F., 40 HOURS

| Base Oil | ΔNN | ΔKV | Pb Loss, mg | Sludge |
|---|---|---|---|---|
| Total Reaction Product | | | | |
| Base oil + 1 wt % solid product | 6.4 | 27 | 2.6 | Heavy |
| Cyclohexane Extract | | | | |
| Base oil + 1 wt % extract | 2.2 | 19 | — | Heavy |
| Base oil + 0.5 wt % extract | 1.8 | 20 | 0.2 | Heavy |
| Base oil + 0.25 wt % extract | 1.9 | 19 | — | Heavy |
| Example 4 | | | | |
| Total Reaction Product | | | | |
| Base oil + 0.5 wt % product | 1.9 | 14 | 8.3 | Heavy |
| Base oil + 0.25 wt % product | 5.6 | 25 | 8.5 | Heavy |
| Filtered Reaction Product | | | | |
| Base oil + 2 wt % filtered product | 0.5 | 10 | 2.7 | Heavy |
| Base oil + 1 wt % filtered product | 1.2 | 8 | 2.9 | Moderate |
| Base oil + 0.5 wt % filtered product | 1.8 | 13 | 5.0 | Moderate |
| Petroleum Ether Extract | | | | |
| Base oil + 2 wt % extract | 0.7 | 5 | 1.3 | Moderate |
| Base oil + 1 wt % extract | 1.8 | 6 | 2.3 | Moderate |
| Base oil + 0.5 wt % extract | 1.8 | 7 | 8.7 | Moderate |
| Cyclohexane Extract | | | | |
| Base oil + 1 wt % extract | 2.1 | 19 | 4.2 | Heavy |
| Base oil + 0.5 wt % extract | 1.8 | 13 | 3.9 | Moderate |

As shown by the data presented in Table 1, the oxidative stability of the base oil is markedly improved by the addition of the reaction products and fractions thereof of the present invention.

For the copper corrosion test, the reaction products were blended into a refined mineral base oil which contained 3% sulfurized isobutylene. The blends were then evaluated in the ASTM D-130 test. In general the test involves immersing a polished copper strip in the oil blend and heating for 6 hours at 212° F. At the end of this period the strip was removed, washed and compared with ASTM Copper Strip Corrosion Standards. The results are presented in Table 2.

TABLE 2

| ASTM D-130 Copper Corrosion Test | |
|---|---|
| Base Oil | Rating |
| Base oil alone | 3B |
| Example 4 | |
| Total Reaction Product | |
| Base oil + .25 wt % product | 2A |
| Filtered Reaction Product | |
| Base oil + .5 wt % filtered product | 1B |
| Base oil + .25 wt % filtered product | 2A |
| Petroleum Ether Extract | |
| Base oil + .5 wt % extract | 3A |
| Cyclohexane Extract | |
| Base oil + .5 wt % extract | 2C |

A rating of 1A or 1B denotes degrees of slight tarnish; a rating of 2A, 2B, 2C, 2D and 2E denotes degrees of moderate tarnish; a rating of 3A or 3B denotes degrees of dark tarnish and a rating of 4A, 4B or 4C denotes degrees of severe corrosion.

Thus, the results presented in Table 2 demonstrate the efficacy of the reaction products of the present invention in reducing copper corrosion.

I claim:

1. A lubricant composition which comprises an oleaginous material and, in an amount effective to impart corrosion prevention and antioxidation properties thereto, the reaction product of (1) a benzotriazole compound having the formula:

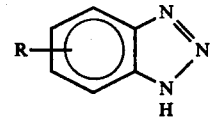

where R is hydrogen or a hydrocarbyl group containing 1 to about 12 carbon atoms and (2) an organic sulfur containing compound selected from the group consisting of α and β substituted allyl sulfides, α and β substituted allyl disulfides, and sulfurized olefins having reactive unsaturated bonds.

2. The composition of claim 1 wherein said α and β substituted allyl sulfides and disulfides have the formula:

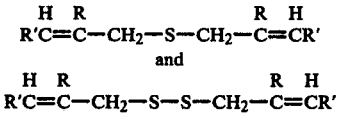

where R and R' are selected from the group consisting of hydrogen, alkyl having from 1 to about 8 carbon atoms, aryl and aralkyl having from 6 to about 14 carbon atoms.

3. The composition of claim 2 wherein R and R' are selected from the group consisting of hydrogen, alkyl having from 1 to about 4 carbon atoms, aryl and aralkyl having from 6 to about 12 carbon atoms.

4. The composition of claim 2 wherein said α and β substituted allyl sulfides and disulfides are selected from the group consisting of allyl sulfide, allyl disulfide, methallyl sulfide, methallyl disulfide, propallyl sulfide, propallyl disulfide, phenallyl sulfide and phenallyl disulfide.

5. The composition of claim 2 wherein said α and β substituted allyl sulfide is methallyl sulfide.

6. The composition of claim 2 wherein said α and β substituted allyl disulfide is methallyl disulfide.

7. The composition of claim 1 wherein said sulfurized olefin is sulfurized isobutylene.

8. The composition of claim 1 wherein said benzotriazole compound is reacted with said organic sulfur containing compound in the presence of an acid catalyst.

9. The composition of claim 1 wherein said benzotriazole compound is reacted with said organic sulfur containing compound at molar ratios of benzotriazole compound/organic sulfur containing compound of from 0.25/1 to about 10/1.

10. The composition of claim 1 wherein said benzotriazole compound is reacted with said organic sulfur component at temperatures from about 5 to 150° C.

11. The composition of claim 1 wherein said reaction product is present in an amount from 0.1 to 10 weight percent of the total composition.

12. The composition of claim 1 wherein said reaction product is present in an amount from 0.25 to 5 weight percent of the total composition.

13. The composition of claim 1 wherein said oleaginous material is selected from the group consisting of mineral oils, synthetic oils and greases thereof.

14. The composition of claim 1 wherein said benzotriazole compound is benzotriazole and said organic sulfur containing compound is methallyl sulfide.

15. The composition of claim 1 wherein said benzotriazole compound is benzotriazole and said organic sulfur containing compound is methallyl disulfide.

16. The composition of claim 1 wherein said benzotriazole compound is benzotriazole and said organic sulfur containing compound is sulfurized isobutylene.

17. The composition of claim 1 wherein a fraction of said reaction product is utilized.

18. A reaction product of (1) of benzotriazole compound having the formula:

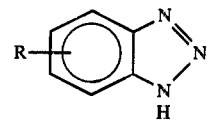

where R is hydrogen or a hydrocarbyl group containing from 1 to about 12 carbon atoms and (2) an organic sulfur containing compound selected from the group consisting of $\alpha$ and $\beta$ substituted allyl sulfides, $\alpha$ and $\beta$ substituted allyl disulfides, and sulfurized olefins having reactive unsaturated bonds.

19. The reaction product of claim 18 wherein said benzotriazole compound is reacted with said organic sulfur containing compound in the presence of an acid catalyst.

20. The reaction product of claim 18 wherein said benzotriazole compound is reacted with said organic sulfur containing compound at molar ratios of benzotriazole compound/organic sulfur containing compound of from 0.25/1 to about 10/1.

21. The reaction product of claim 18 wherein said benzotriazole compound is reacted with said organic sulfur component at temperatures from about 5° to 150° C.

22. The reaction product of claim 18 wherein said benzotriazole compound is benzotriazole and said organic sulfur containing compound is methallyl sulfide.

23. The reaction product of claim 18 wherein said benzotriazole compound is benzotriazole and said organic sulfur containing compound is methallyl disulfide.

24. The reaction product of claim 18 wherein said benzotriazole compound is benzotriazole and said organic sulfur containing compound is sulfurized isobutylene.

* * * * *

UNITED STATES PATENT AND TRADEMARK OFFICE
CERTIFICATE OF CORRECTION

PATENT NO. : 4,153,563
DATED : May 8, 1979
INVENTOR(S) : MILTON BRAID

It is certified that error appears in the above-identified patent and that said Letters Patent are hereby corrected as shown below:

Column 1, line 22, "b 3,413,227" should read --3,413,227--.
Column 2, line 41, "enire" should read --entire--.
Column 5, line 1, "pahy" should read --aphy--.
Column 5, line 22, "as" should read --was--.
Column 9, line 1, Claim 18, "(1) of" should read --(1) a--.

Signed and Sealed this

Eleventh Day of September 1979

[SEAL]

Attest:

LUTRELLE F. PARKER
*Attesting Officer*  *Acting Commissioner of Patents and Trademarks*